United States Patent [19]
Howard

[11] Patent Number: 5,889,055
[45] Date of Patent: Mar. 30, 1999

[54] L-CARNITINE AND ACETYL-L-CARNITINE COMBINED FOR PREVENTION AND TREATMENT OF SYNDROMES RELATED TO DISEASES OF ENERGY METABOLISM

[76] Inventor: James R. Howard, Box 191, Brawley, Calif. 92227

[21] Appl. No.: 826,555

[22] Filed: Apr. 4, 1997

[51] Int. Cl.$^6$ .................................................. A01N 37/12
[52] U.S. Cl. ............................................................ 514/561
[58] Field of Search .............................................. 514/561

[56] References Cited

U.S. PATENT DOCUMENTS

| | | |
|---|---|---|
| 4,346,107 | 8/1982 | Cavazza et al. . |
| 4,599,232 | 7/1986 | Bertelli . |
| 5,576,384 | 11/1996 | Nolken et al. . |

OTHER PUBLICATIONS

Luft: "The development of mitochondrial medicine," *Proc. Natl. Acad. Sci USA*, vol. 91, pp.8731–8738, Sep. 1994.

Singh et al. "Mitochondrial Genome Mutations and Kidney Disease," *American Journal of Kidney Diseases*, vol. 28, No. 1 (July), 1996; pp. 140–146.

Shishido et al: "Cerebral oxygen and glucose metabolism and blood flow in mitochondrial encephalomyopathy: a PET study," *Neuroradiology* (1996) 38:pp. 102–107.

Pons et al: "Primary and Secondary Carnitine Deficiency Syndromes," *Journal of child Neurology*, vol. 10, Supplement No. 2, Nov. 1995, pp. 2S9–2S24.

Castorina et al: "Acetyl–L–Carnitine Affects Aged Brain Receptorial System in Rodents," *Life Sciences*, vol. 54, No. 17, pp. 1205–1214, 1994.

Carta et al: "Acetyl–L–Carnitine and Alzheimer's Disease: Pharmacological Considerations Beyond the Cholinergic Sphere," *New York Academy of Science*, pp. 324–326.

Aureli et al: "Aging brain: effect of acetyl–L–carnitine treatment on rat brain energy and phospholipid metabolism. A study by $^{31}$P and $^1$H NMR spectroscopy," *Brain Research*, 326 (1990), pp. 108–112.

Stanley: "Carnitine Disorders," *Advances in Pediatrics*, vol. 42, 1995, pp. 209–242.

Shoubridge: "Mitochondrial DNA Diseases: Histological and Cellular Studies," *Journal of Bioenergetics and Biomembranes*, vol. 26, No. 3, 1994, pp. 301–310.

Zeviani et al: "Mitochondrial myopathies," *Current Opinion in Rheumatology* 1994, pp. 559–567.

Sisson et al: "Myocardial Diseases," *Textbook of Veterinary Internal Medicine*, Chapter 96, pp. 995–1005.

Kittleson et al: "Results of the Multicenter Spaniel Trial (MUST): Taurine–and Carnitine–Responsive Dilated Cardiomyopathy in American Cocker Spaniels with Decreased Plasma Taurine Concentration," *Journal of Veterinary Internal Medicine*, vol. 11, No. 4 (Jul.–Aug.), 1997, pp. 204–211.

Bremer: "Carnitine—Metabolism and Functions," *Physiological Reviews*, vol. 63, No. 4, Oct. 1983, pp. 1420–1456.

*Primary Examiner*—Keith D. MacMillan
*Attorney, Agent, or Firm*—Nixon & Vanderhye P.C.

[57] ABSTRACT

A combination can be of L-carnitine and acetyl-L-carnitine administered orally or as parenteral injection in domesticated animals, especially pet animals, and humans for prevention or treatment of syndromes or diseases arising from dysfunctional energy metabolism. Syndromes involving skeletal and cardiac muscle benefited from L-carnitine, syndromes related to the central nervous system improved with acetyl-L-carnitine. Although the two cofactors do not substitute metabolically for each other effects of the combination are found to be synergistic.

20 Claims, No Drawings

L-CARNITINE AND ACETYL-L-CARNITINE COMBINED FOR PREVENTION AND TREATMENT OF SYNDROMES RELATED TO DISEASES OF ENERGY METABOLISM

BACKGROUND OF THE INVENTION

The present invention relates to dysfunctional energy metabolism of both glucose and lipids in animals and humans. More particularly, a novel combination of metabolic cofactors, L-carnitine combined with acetyl-L-carnitine, restores normal mental and physical activity to aged patients with dysfunctional energy metabolism and, when employed prophylactically, prevents development of related syndromes.

In the normal course of aging an organism's ability to synthesize, conserve, and absorb crucial metabolic cofactors declines. Conversion of nutrients to useful energy within cells involves highly specific enzymatic processes which are sensitive to presence or absence of these cofactors. In the higher order of animals, especially with respect to humans, as well as laboratory rodents, enzyme pathways of energy metabolism are known with relative precision. Despite extensive research efforts, however, interrelationship of many metabolic processes and enzymatic cofactors remain imprecisely known. Indeed, metabolic interrelationships of enzymatic cofactors L-carnitine and acetyl-L-carnitine in cardiac and skeletal muscle have not been completely defined. The same is true in nervous tissue, especially the brain, where available research data concerning function of these cofactors are often contradictory and inconclusive owing to the inordinate difficulty in establishing truly controlled experimental formats. Much of what is known has been gained from the organ's response to traumatic, toxic, and ischemic insults as well as investigations of these cofactors' effects in chronically diseased brains. Such information provides little or no guidance to those concerned with psychophysiologic and psychomotor disturbances or confronting syndromes affecting multiple tissues. The following brief notations are believed to illustrate the complexity of the state of the art knowledge of diseases of energy metabolism.

The study of disease of energy metabolism commonly referred to as mitochondrial diseases is an emerging specialty in human medicine. Most of these diseases arise from mutation of the mitochondrial genomes and, to a lesser extent, nuclear genes. Such mutations result in specific dysfunctional enzymes in metabolic pathways and in structural changes of mitochondria which disrupt enzyme orientation in metabolic pathways thereby impairing their efficiency. Mitochondrial genome mutations may exist at birth but typically occur over time as base dilutions, substitutions, and insertions during the course of replication; or in response to environmental factors, disease, and accumulation of toxic metabolites. Clinical syndromes presented depend upon the metabolic pathway affected and the proportion of dysfunctional mitochondria that has been attained. Organs normally effected by disease of energy metabolism are highly differentiated, nonregenerating tissues requiring high levels of oxygen and energy, such as brain and skeletal and heart muscle. Treatment of these diseases is directed to sustaining life by supplementing high levels of metabolic cofactors in an effort to skew metabolism along specific pathways and to providing substrates for the pathways. Rarely, in human medicine, do deficiencies of cofactors or substrates cause diseases of energy metabolism. In veterinary medicine only a few genetically based diseases of energy metabolism are recognized. Among them are dilated cardiomyopathy in dogs and stress syndrome in swine. However, deficiencies of metabolic cofactors in dogs have been investigated. A study of commonly encountered age-related syndromes in old dogs, examples of which are included in this application, revealed them to be due to dysfunctional energy metabolism. More specially, syndromes involving heart and skeletal muscle were relieved by L-carnitine supplemention while a syndrome affecting the brain was relieved by increased acetyl-L-carnitine intake. However, complex interrelationships exist. For example, a treatment for a psychotic syndrome with acetyl-L-carnitine was successful but resulted in emergence of a heart failure syndrome and both cofactors were required to normalize the dog. In another case, synergistic effects were realized with the two cofactors combined as opposed to their individual use in treating a syndrome involving skeletal muscle. And, in yet another case, a dog that heretofore had required heavy sedation to control an epileptic syndrome, experienced unexpected improvement in after it had been treated with combined L-carnitine and acetyl-L-carnitine for several weeks.

L-carnitine as well as acetyl-L-carnitine are natural constituents of higher organisms, particularly animal heart and muscle tissue and can be synthesized by the body or obtained from red meat, poultry, fish, and dietary products. L-carnitine is absorbed from the small intestine into systemic circulation at a rate of about 2 to 5 mg per pound body weight which is compatible with normal physiologic function and the basis for dosages in the accompanying studies. In standard medical treatment of syndromes related to deficiency of L-carnitine or L-carnitine-dependent enzymes dosage of L-carnitine employed may be 10 to 50 times higher than rate of physiologic intestinal absorption. This affords passive diffusion of carnitine into systemic circulation but such high dosages have the risk of causing diarrhea.

L-carnitine (3-hypodroxy-4-N-trimethylaminobutyric acid) has two main functions, both critical to energy metabolism. The first is translocation of long-chain fatty acids from the cytosol across the outer and inner mitochondrial membranes and intervening space into the mitochondrial matrix. The second function is to modulate intracellular CoA homeostasis within the mitochondrial matrix by transesterifation of acyl-CoA esters produced in B-oxidation which regenerates CoA and acylcarnitine. Accumulation of long chain acyl-CoA esters is a consequence of enzyme disfunction and metabolic impairment or stasis in the B-oxidation system. Resulting shortage of available CoA then limits transfer of acetyl groups to the Krebs cycle for energy production. Acylcarnitine, produced during homeostasis, can be exchanged across the mitochondrial membrane for free carnitine and eventually transported out of the cell to be excreted in urine. Canids are unique in the fact that their liver and kidneys synthesize carnitine but they lack an enzyme in skeletal and cardiac muscle which is crucial to the last stage of L-carnitine synthesis. In dogs L-carnitine is synthesized in the liver and transported to muscle tissue.

Acetyl-L-carnitine (-trimethyl-B-acetylbutyrobetaine) shares intracellular CoA homeostatic function with carnitine. It is the prevalent ester of carnitine in tissue, freely exchangeable across subcellular membranes, and can serve as a pool of acetyl groups to regenerate acetyl-CoA. This property comes into play in instances of excessive exercise where glycolysis has resulted in accumulation of lactic acid in muscle cells. Studies with rat brain tissue show acetyl-L-carnitine to be associated with increased glycolysis and oxygen metabolism. Other studies indicate acetyl-L- carnitine enhances ketone-body metabolism in rat brains. In experimentation with rats acetyl-L-carnitine has been shown to maximize energy production, promote membrane stability, restore membrane changes that are age-related, and serve as precursor to acetylcholine. Cholinergic effects enhance nerve impulse transmission and have been demonstrated to counter or delay age-changes and dementia in brains of rodents and humans.

In addition to depleted available energy and concomitant depression of cell and organ function another consequence of impaired energy metabolism is formation of free oxygen radicals and their destructive effects on proteins and other large molecules, mitochondrial membranes, and especially mitochondrial DNA. Environmental sources of free radicals are infection, drugs, hypoxia, chemicals, and food. These destructive effects are cumulative leading to development of physiologic dysfunctions with increasing age, and along with mitochondrial genome mutation from other causes, must be considered as contributors to the etiology of syndromes seen with the dogs in this report. Normally, cell and organ function deteriorates with age resulting in reduced biosynthesis of metabolites and cofactors, reduced digestive function and enteral absorption, and impaired renal tubule resorption from glomerular filtrate. In elderly dogs any or all of the above can lead to depletion of tissue reserves of L-carnitine and acetyl-L-carnitine to the extent that energy metabolism is impaired.

Four syndromes, psychosis, skeletal muscle weakness and atrophy, epileptiform convulsions, and cardiomyopathy were observed in dogs in this study. Syndromes presented as singular entities as in the skeletal muscle syndrome or as complex of syndromes. Psychosis, in the form of extreme anxiety with trembling, hiding and panicky flight are common in old dogs exposed to sharp noises such as fireworks discharges. Even a mild stimulant such as the sound of cellophane being crumbed into a ball will illicit a panic response in some dogs. Management of most such cases is with tranquilizers during periods when stimuli are most prevalent (e.g. New Years Eve and The Fourth of July). Tranquilizers do nothing to cure the patient, their effect is psychological depression. When patients become extremely debilitated by the psychosis mood altering drugs such as doxepin and fluoxetine can be employed. Here again a cure will not be forth coming. At best the animal will be so heavily sedated as to not pose a threat to itself, property, or the public. Pharmacologically-active mind-depressions do not correct any metabolic imbalances in the brain, hence do not effect a cure. In some cases psychotic episodes progress to grand mal seizures. Depressant drugs are the common means employed for their control. Phenobarbital, primidone, and/or KBr are consumed once to several times a day. The drugs do not correct the underlying metabolic dysfunction in the brain but they do stop the seizures at the expense of greatly depressing the patient. Psychotic and seizuring dogs are not demented in the sense that there is large-seal neuronal dysfunction with loss of inelegance, memory, or awareness of surroundings. Psychoses are almost the opposite, with heightened awareness of sounds and events in the environment. They may precipitate seizures.

Among the causes of skeletal muscle weakness and reduction of mass are nutritional deficiency, in particular deficiency of SE and vitamin E. In cases of nutritional myopathy, refined to as white muscle disease, the vitamin E interrelates metabolically with SE and can be a valuable adjust to therapy. This condition is common to herbivorous and omnivorous but not carnivorous. A myopathy common in dogs is denervation myopathy, a condition that develops secondary to herniation of intervertebral dises and ankylosing spondyloarthropathy. Where spinal nerves are damaged reduced impulse stimulation to the innervated muscle leads to weakness, degeneration, and atrophy. This form of muscle disease is managed by attempting to reduce trauma to the spinal nerve by controlling chronic inflammation and bone formation along the nerve's course from the spine with drugs classified as non-steroidal anti-inflammatory agents. If skeletal muscle is not exercised it will become weak and degenerate and eventually atrophy. This condition, common to traumatic injuries, precludes normal function after extended periods of time. There are auto-immune myopathies where the body produces an immune reaction, usually to some infectious agent, that cross reacts with skeletal muscle. Management of these conditions is based upon suppression of the immune reaction for an undetermined period of time. Eventually, the reaction subsides and the immune depressant drugs can be withdrawn. There are other causes of skeletal muscle weakness and atrophy. Clinically they are morphologically similar to one and other and require biopsy for definitive diagnosis.

Heart failure secondary to dilated cardiomyopathy has been treated with high dosages of L-carnitine, 100 mg per pound body weight. Such massive therapy is only moderately successful, at best. In most cases prognosis is very guarded. One reason for the poor response may be that diagnosis is not forthcoming until pathology is so advanced it cannot be reversed. Another consideration is that L-carnitine therapy only addresses lipid metabolism in the heart ignoring the part glycolysis may contribute. Cardiac arrhythmias are part of heart failure and evidence of pathology of heart muscle. Arrhythmias are treated with pharmachologically active drugs which may stabilize the heart. Drugs such as lidocaine, propanalol, digoxin, and procainamide all are useful in stabilizing the heart beat which may be critical at times but such drugs do not address the metabolic disturbance that caused the pathology. It is common for dogs with cardiac arrhythmias to die suddenly or, at best, be forced to remain on medication for extended periods, even for life.

As a consequence of above-noted complexities in identifying and treating syndromes related to dysfunctional energy metabolism as well as understanding their interrelationships little progress has been achieved in prevention and therapy. The following examples of U.S. Patents relating to carnitine and acetyl-L-carnitine are illustrative of the existing state of the art.

U.S. Pat. No. 4,346,107 relates specifically to the use of acylcarnitine in treating dementia of human patients particularly when mental dysfunction is related to impaired cerebral blood flow. Typifying numerous approaches to management of dementias, is does not investigate psychoses and epileptiform seizures as being associated with deficits of energy metabolism, their connection with deficiencies of L-carnitine and acetyl-1-carnitine, the possibility of precipitating other energy deficit syndromes as a consequence of therapy with a single metabolic cofactor, and the need for therapy that modulates both glycolyses and lipid metabolism.

U.S. Pat. No. 4,599,232 relates to combination of carnitine or acetylcarnitine and coenzye Q10 for tissue metabolic disorders involving circulatory function. The patent's use of coenzymes Q10 directs its effects towards control of free radical excess and facilitation of oxidative phosphorylation, the final stage of energy metabolism. It does not address the observed synergistic effects of combined L-carnitine and acetyl-L-carnitine on glycolysis and lipid metabolism nor does it recognize the need of both metabolic cofactors when treating dysfunctional energy metabolism related to deficit of L-carnitine or acetyl-L-carnitine as discovered in the present patent.

U.S. Pat. No. 5,576,384 relates to the general use of acylcarnitine for therapy of patients with Acylcarnitine Metabolic Dysfunction Syndrome. It excludes consideration of carnitine metabolism disorders and the combined therapy for disorders where both deficiencies may exist.

Following are references pertaining to diseases of energy metabolism their causes and treatments.

Luft, R. The development of mitochondrial medicine. Proc. Natl. Acad. Sci. USA 1994; 91:8731–8738

Singh P J, Santella R N, Zawada E T. Mitochondrial Genome mutations and kidney disease. Am. Jour. of Kid. Dis. 1996; 28: 140–146

Shishido F, Uemura K, Inugami A, Tomura N, Higano S, Fujita H, Sasaki H, Kanno I, Mura Kami M, Watahiki Y, Nagata K. Cerebral oxygen and glucose metabolism and blood flow in mitochondrial encephalopathy: a PET study. Neurorad. 1996; 38: 102–107

Pons R, DeVito DC. Primary and secondary carnitine deficiency syndromes. Jour. Child Neuro. 1995; 10: 258–2524

Castorina M, Ferraris L. Acetyl-Carnitine affects aged brain receptorial system in rodents. Life Sci. 1994; 54: 1205–1214

Carta A, Calvani M, Bravi D, NiBhuach alla S. Acetyl-L-Carnitine and Alzeimer's disease: pharmacological considerations beyond the cholinergic sphere. N.Y. A cad. of Sci. 324–326

Aureli T, Miccheli A, Ricciolini R, DiCocco ME, Ramacci MT, Angelucci L, Ghirardi O, Cont F. Aging brain: effect of Acetyl-L-Carnitine treatment on rat brain energy and phospholipid metabolism. A study by 31P and 'HNMR spectroscopy. Brain Res. 1990; 526: 108–112

Stanley C. Carnitine disorders. Adv. in Ped. 1995; 42: 209–242

Shoubridge E A. Mitochondrial DNA disease: Histological and cellular studies. Jour Bioenerg. and Biomemb. 1994; 28: 301–310

Zeviani M, Amati P, Savoia A. Mitochondrial Myopathies. Curr. Opin. Rheum. 1994; 6: 559–567

Sisson D D, Thomas W P. Myocardial diseases. In: Ettingen S J, Feldman E C, ed. Textbook of Veterinary Internal Medicine. 4th ed. Philadelphia: W B Saunders, 1995: 995–1005

BRIEF SUMMARY OF THE INVENTION

The present invention, A novel combination of L-carnitine and acetyl-L-carnitine, has been discovered to relieve syndromes related to mutations of mitochondrial genomes and age-related impairment of energy metabolism due deficiencies of L-carnitine and acetyl-L-carnitine in domesticated animals.

The invention in its various forms are easy to prepare. Liquids for oral use are prepared at room temperature by dissolving prescribed quantities of crystalline forms of the cofactors in water, adding preservative and coloring and/or flavoring, filter sterilizing, and bottling. Liquid for injection is prepared at room temperature by dissolving prescribed amounts of each cofactor in water. If the material is to be dispensed in a multi-dose vial, preservative is added before the pH is adjusted with NaOH to neutrality and the solution is filter sterilized and bottled. Dry forms of the invention are prepared by mixing prescribed amounts of the two desiccated cofactors. If the invention is to be encapsulated, an anticaking agent to facilitate production may be added prior to encapsulation. If the dry preparation is to be dissolved for intravenous injection the desecrated powder or crystalline mixture is measured into glass vials, sealed and sterilized.

Specific quantities of L-carnitine and acetyl-L-carnitine provided in the aqueous solutions of the invention may be varied depending upon projected use. As an example, it is within the comprehension of the invention that solutions may be prepared to allow each milliliter thereof to contain: from about 0.1 to 400 milligrams L-carnitine and 0.1 to 400 milligrams acetyl-L-carnitine. Similarly, ratios of carnitine to Alcar in powdered forms can be varied from 1 to 100 depending upon intended usages.

All preparations of the invention are easy, safe and convenient to use. The liquid for oral consumption can be taken directly into the mouth and swallowed or measured into it with a spoon, dropper, syringe, or like device. Similarly, the liquid preparation can be measured into food or drink for consumption. The usual, standardized techniques for parenteral injection of drug with hypodermic needle and syringe is to be employed for administering the injectable format of the invention subcutaneously, intramuscularly, intravenously, or as an additive to compatible liquid medicaments designed for intravenous injection.

Among the preferred forms of the invention is a solution formulated to contain 45mg L-carnitine and 45 mg acetyl-L-carnitine per milliliter. Such a preferred solution is particularly useful for oral administration at a dosage level to provide from about 2 to 4 milligrams of each cofactor per pound of body weight. The invention is beneficial in aleaveating symptoms when added to the food of psychotic domesticated animals, those with cardiomyopathy or skeletal muscle weakness or atrophy, those with tendency to have epileptiform seizures or in aged obese or debilitated animals when these conditions are due to inadequacy of available L-carnitine and/or acetyl-L-carnitine. This preferred form of the invention is particularly useful for supplementing the diet at a rate of about 5 milligram per pound of body weight on a daily basis to prevent development of such as cardiomyopathy, skeletal muscle weakness or atrophy, psychosis, some forms of epilepsy, and to generally improve mental and physical activity and well-being.

The purpose of the invention is to treat or prevent from developing disease syndromes related to inadequate tissue levels of L-carnitine and/or acetyl-L-carnitine and to treat or prevent disease syndromes related to mutations of mitochondrial DNA, changes in mitochondrial structure, and deterioration of the body's ability to synthesize, conserve, and absorb L-carnitine and acetyl-L-carnitine. One severely psychotic dog had been unsuccessfully treated for about one year with two different mood-altering drugs commonly used for treatment of such mental derangements. The owner, committed to euthanasia, agreed to a final effort to save the animal; the novel and untested use of acetyl-L-carnitine to treat psychosis. Response was prompt, recovery began in two days. The effects of acetyl-carnitine on brain function appeared to correct the dog's psychosis. But when the dog became normal mentally, acute circulatory failure developed. L-carnitine was substituted for acetyl-L-carnitine and the circulatory failure was resolved. Shortly, however, the psychosis resumed. L-carnitine and acetyl-L-carnitine were not metabolically interchangeable in this case. A novel, treatment was initiated. L-carnitine and acetyl-L-carnitine were combined and administered in the dog's food, 5 mg per pound body weight. He promptly became normal and remained, so receiving daily supplementation with the invention. This case demonstrated that, with diseases of energy metabolism, some syndromes may be subclinical only to be expressed in time or when a more prominent syndrome is relieved, increased activity may bring an underlying syndrome to light. Or, when treating a syndrome with one cofactor, in this case acetyl-L-carnitine, a disturbance in metabolism may develop in another organ necessitating the other cofactor, L-carnitine. It is clear that when treating diseases of energy metabolism in old dogs combined L-carnitine and acetyl-L-carnitine are in order.

This principle was underscored by a dog treated with L-carnitine for skeletal muscle atrophy, weakness and pain. It responded, functioning normally in three weeks. Then acetyl-L-carnitine was substituted for L-carnitine to observe any cross-effectiveness. No cross-effect was observed. Shortly, symptoms of muscle weakness and pain resumed. The cofactors were mixed, as in the powdered preparation of the invention, and added to the dog's food, 5 mg per pound body weight. Within one week she was normal. This accelerated response compared with the time of response when treatment was with L-carnitine alone would suggest metabolic synergism exists between L-carnitine and acetyl-L-carnitine.

A third case demonstrated effectiveness of combined L-carnitine and acetyl-1-carnitine for treating skeletal muscle weakness and neurologic symptoms. Both syndromes had been long standing in an old dog that was presented with acute circulatory failure. The dog's heart disease was diagnosed as being early cardiomyopathy without marked enlargement. When treated with procainamide and the invention at a rate of 5 mg of combined 1-carnitine and acetyl-L-carnitine per pound of body weight the initial arrhythmia was converted over night. After one week the procainamide therapy was stopped the heart continued to improve as the dog received the invention on a daily basis and within a month the electrocardiogram was normal. This was an unprecedented response, for most such cases die within a few days. It is assumed the invention was instrumental in correcting the metabolic imbalance causing the cardiomyopathy.

L-carnitine and acetyl-L-carnitine are biochemically interchangeable in mitochondria through action of the enzyme carnitine acetyl-transferase. However, evidence in the studies reported herein indicate distinct differences in metabolic function of the two cofactors with no apparent cross reaction or substitution between them. It is well accepted that L-carnitine effects are primarily on energy metabolism of lipids. However, metabolic pathways involving acetyl-L-carnitine are not well defined. The following may explain how the psychotic dog was benefitted: Research indicates acetyl-L-carnitine enhances glycolysis, oxygen metabolism and energy production in the brain. Which may partially explain beneficial effects observed. Studies of humans with a mitochondrial disease, MELAS, suggest symptoms and lesions are the result of lactic acid accumulation in the brain with concomitant brain edema. Stressful events lead to increase demand for energy in the brain but with limited reserves of acetyl-L-carnitine glycolysis is impeded and lactic acid accumulates. To measurably increase glycolysis, acetyl-L-carnitine facilitate metabolism of pyruvate, making more energy available for cell function and limiting accumulation of lactic acid with its detrimental effects. This same mechanism, acetyl-L-carnitine facilitated pyruvate metabolism, explains the synergism elicited by L-carnitine and acetyl-L-carnitine, the invention was used to treat dogs with skeletal muscle weakness and pathology. Treatment of cardiomyopathy with the invention at physiological levels, mg per pound body weight, more successful than when L-carnitine alone is given even at dosages 20 times higher. Although L-carnitine dependant lipid metabolism is the major energy source in muscle, acetyl-L-carnitine dependant glycolysis is essential to normal muscle cell function.

The invention was superior to conventional therapy for treating the following syndromes that arose from disturbances of energy metabolism:

Psychotic behavior was eliminated and the affected dog regained demeanor and activity level similar to three years previously while its diet was supplemented daily with mg of the invention per pound body weight. It showed no evidence of depression or sedation associated with conventional therapy.

Similarly, a dog with long standing epileptiform seizures, controlled by heavy dosages of KBr had only one mild seizure a month during diet supplementing with the invention at mg per pound of body weight daily. Without KBr therapy.

Two dogs with profound skeletal muscle weakness became fully active while receiving diet supplemention with mg of the invention per pound of body weight each day. One dog regained the ability to jump into a pickup truck. This patient had a previously-undescribed myopathy diagnosed from a biopsy as a degenerative condition probably related to dysfunctional energy metabolism. Other more traditional therapies for treating the myopathy were ineffective. The other dog was able to run freely and chase cats, previous to treatment it had to be supported with a sling under its belly when walking more than a few feet.

Two dogs with circulatory failure recovered completely during the course of daily diet supplementation with mg of the invention per pound of body weight. The dogs had a brief course of oral treatment with procianamide. The superiority of invention was manifested in the completeness of recovery without prolonged anti-arrhythmia therapy.

Other aspects and advantages of the present invention will be apparent upon consideration of the following detailed description thereof.

DETAILED DESCRIPTION OF THE INVENTION

The term "cofactor" in general refers to carnitine, Alcar, other vitamins, and trace minerals that facilitate chemical reactions with specific enzymes in cells. "Parenteral" shall mean any administrative mode other than oral and shall include subcutaneous, intramuscular and intravenous injection. "Syndrome" is a set of symptoms, or complex of symptoms occurring together which may or may not characterize a specific disease entity. "Carnitine and Alcar responsive syndrome" shall represent a symptom complex which is benefited by amelioration of symptoms toward the normal through treatment of the patient with carnitine and acetyl-L-carnitine.

The purpose of the invention is to treat, or prevent from developing, disease syndromes related to inadequate tissue levels of one or both metabolic cofactors, and to treat or prevent disease syndromes related inadequate intake of L-carnitine or acetyl-L-carnitine, or to mutations of mitochondrial DNA, changes in mitochondrial structure, and deterioration of the body's ability to synthesize, conserve and absorb L-carnitine and acetyl-L-carnitine.

EXAMPLE 1

This example relates to the preparation of one liter of a stable acqueous solution containing, per milliliter, 45 mg L-carnitine and 45 mg acetyl-L-carnitine. All procedures are carried out at room temperature unless otherwise indicated.

A solution is prepared by dissolving 45 grams of 1-carnitine in 500 ml water. To this solution 45 grams of acetyl-1-carnitine are added and dissolved.

A second solution is made by dissolving 1 gram of methyl paraben in 400 milliliters water. Dissolution can be hastened by warming the water to 40 degrees centigrade and stirring constantly. The solutions are cooled to room temperature and water is added sufficient to bring the final quantity to 1000 milliliters. The final solution is filtered to remover any and all bacteria, and like-sized microbes. This sterile solution is dispensed in sterile bottles.

This solution has a mildly acidic taste that enhances many food flavors it is intended for oral administration or to be added to the diet or drinking water of an individual animal at the rate of one milliliter per fifteen pounds body weight.

EXAMPLE 2

This example relates to preparation of one liter of sterile, neutral, stable aqueous solution containing, per milliliter, 16.7 mg carnitine and 16.7 mg acetyl-L-carnitine. All procedures are carried out at room temperature.

A solution is prepared by dissolving 16.7 grams of L-carnitine in 400 milliliters of distilled, pyrogen free water. When it is dissolved 16.7 grams acetyl-L-carnitine is added to the solution and is dissolved.

A second solution is made by dissolving 1 gram of methyl paraben in 400 milliliters water. Dissolution can be hastened by warming the water to 40 degrees centigrade and stirring constantly. The second solution is mixed with the first solution.

The pH of the mixed solutions is adjusted to neutrality with approximately 2.95 grams NaOH. Sufficient quantity water is added to bring the final volume to 1000 milliliters and the solution is filtered through sterile equipment to remove bacteria and like-sized microbes. It is then bottled in sterile rubber-stopped glass vials.

This solution is intended for subcutaneous, intramuscular or intravenous injection at the rate of 1 ml per 15 pounds body weight. To provide the added quality of being useful in animals unable to consume or retain injested materials and in instances where rapidity of response to therapy may be critical for the life or well being of the patient.

EXAMPLE 3

This example relates to preparation of desiccated powder containing equal amounts of the L-carnitine and acetyl-L-carnitine.

The mixture is prepared by combining and uniformly mixing 50 mg of both desiccated L-carnitine and acetyl-L-carnitine in a low moisture atmosphere. An anticking agent may be blended into the mixture to facilitate processing through a capsule filling machine. The choice of anticaking agent must be compatible with state and federal pure food and drug regulations. The powdered preparation is placed in gelatin capsules of a size sufficient to contain 45 mg L-carnitine and 45 mg acetyl-L-carnitine to be swallowed by a 15 pound dog or the capsule may be opened and the contents sprinkled onto or mixed with the patient's food.

EXAMPLE 4

This example relates to preparation of sterile desiccated powder containing equal amounts L-carnitine and acetyl-L-carnitine. The mixture is prepared by combining and uniformly mixing, in a dry atmosphere, 50 grams amounts of desiccated L-carnitine and acetyl-L-carnitine. The mixture is measured in 200 mg amounts into sterile, dry glass ampules which are then sealed. Powder in vials is to be dissolved with sterile water for intravenous use in cases of acute circulatory failure related to L-carnitine and acetyl-L-carnitine responsive cardiopathy or mitochondrial genome mutations where energy metabolism is compromised.

Consistent with the above, oral administration of preparations defined in Examples 1 and 3 were found to be useful in treating pet dogs with cardiomyopathy, skeletal muscle weakness, psychosis and epilepsy. Where these syndromes were actively manifested the preparation eliminated or markedly ameliorated symptoms. When the preparations were discontinued or reduced in amount consumed syndromes recurred. Continued supplementation prevented syndrome development. The following examples relate to the effectiveness of the preparations of the invention.

EXAMPLE 5

A twelve year old male Weimaraner was treated for almost one year for anxiety and trembling. It all began when a minor earthquake one week previous to initial admittance to the hospital resulted in a fearful change in the dog's behavior. Normally placid, following the quake he had trembled uncontrollably when put in his owner's backyard. He was reluctant to enter the hospital and tried to avoid being handled. However, he was not aggressive nor did he show any tendency to bite from fear. Cranial nerve function was normal and clinical examination revealed no physical ailments. It was assumed the dog had a form of anxiety and he was treated with 25 mg of the mood-altering antipsychosis drug doxepin HCl orally once daily. This satisfactorily diminished symptoms for several weeks after which anxiety gradually returned. Six months after starting treatment he was as troubled as when first presented. Medication was changed to 20 mg of another antipsychosis drug fluoxetine HCl orally once daily. Again, anxiety subsided for a few weeks but in time returned and steadily increased in severity. In spite of daily behavior-modifying therapy his mental condition deteriorated to the extent that he voluntarily confined himself and hid behind a couch in one room of the house. Trembling had become violent when he was taken out of doors and he was unable to go on short walks. His food bowl frightened him and he refused to eat unless fed from the owner's hand.

When again brought to the hospital after almost eleven months of therapy with antipsychosis drugs he was very psychotic. His owner had to drag the panicking dog into the waiting room where he trembled and coward under the owner's chair. Clinical examination was much as it was initially. Euthanasia was considered but the owners opted for increasing fluoxetine HCl dosage to 40 mg daily. This gave little relief After two days it was decided to discontinue treatment of the dog with antipsychosis drugs and to investigate a novel therapy. The decision was predicated upon the inventor's personal experience. Having endured depression nightly for more than two decades. The first time he consumed one 500 mg capsules of acetyl-L-carnitine in a "pop culture" effort to improve his memory. Depression ceased! And remained so as long as Alcar was consumed daily. It was thought, there may be a physiologic similarity between depression in humans and psychosis in dogs, the dog's owners agreed to add mg per pound body weight acetyl-L-carnitine orally morning and night to his treatment regimen for one week. The dog's psychosis began to diminish within two days. By the end of the week he no longer hid in the house, would eat from his food bowl, and trembling when he went outside was much less severe. Acetyl-L-carnitine therapy was continued but fluoxetine HCI dosage was reduced to 20 mg orally once daily. His fearfulness continued to diminish and he began to go on short walks. Twenty-one days later symptoms were so minimal that fluoxetine HCI was discontinued. Within a week his behavior and activity level were as normal as they had been three years previously. However, that day, while on a moderately long walk he suddenly collapsed, temporarily became unconscious and, unable to rise or walk, was carried home. The owner commented that on the previous day's walk a similar but less severe episode had taken place.

When examined at the hospital he was conscious but very depressed with no sign of anxiety. His pulse was weak, 200 beats per minute, and capillary refill time was four seconds. An electrocardiogram (ECG) tracing showed no arrhythmia but the T-wave was augmented with negative polarity. Because of symptoms: syncope, exercise intolerance, weak pulse, tachycardia, and prolonged capillary refill time the dog was diagnosed as suffering from cardiac failure. Sustained-release 500 mg procainamide orally morning and night was added to the acetyl-L-carnitine regimen. The following day, an ECG showed improvement. Amplitude of the T-wave was less but polarity was still negative. His demeanor was brighter and he was responsive to owner and surroundings. Within three days he could again walk for short distances without signs of distress. However, his exercise tolerance was sub-normal. It was decided to continue giving him the procainamide, for it seemed to have helped cardiac function, but replace acetyl-L-carnitine with L-carnitine, 5 mg per pound body weight orally morning and night, to see if it might further improve his level of physical activity. Following seven days of L-carnitine supplement, his level of physical activity was again normal and he was going for two-mile long walks. In an attempt to clarify whether the dog's activity level had returned to normal because of carnitine and its metabolic effects on heart muscle or the procainamide and its effect on cardiac impulse conduction, the latter was phased out through the ensuing week. During that time he continued to walk and run normally with no evidence of cardiac insufficiency. This indicated disturbed metabolism of myocardial cells must have caused the circulatory failure for the dog's level of activity improved most when he was given L-carnitine and it remained normal with deletion of procainamide. Daily treatment only with L-carnitine was continued. Then after 17 days without acetyl-L-carnitine, the owner called to report the dog's physical activity was normal but psychosis had returned. It appeared, on one hand, that acetyl-L-carnitine had improved the dog's psychic state but cardiac malfunction developed once his activity level increased. On the other hand, L-carnitine had corrected the circulatory failure without benefiting the psychosis. In an effort to correct the resurging psychotic state while preventing recurrence of heart failure acetyl-L-carnitine and L-carnitine were given to the dog. To evaluate their compatibility the two nutrients were mixed together as powders in equal parts as a dietary supplement to be added as a powder to the dog's food. Dosage was mg per pound body weight daily. While on the combination anxiety symptoms disappeared within five days and no further heart failure signs developed. The nutrient combination was continued and the dog behaved normally, running and playing, with no signs of fear or anxiety for two months after which time he was boarded at the hospital. While at the hospital he was closely observed, and judged to behave and function as normally as when he was three years younger.

EXAMPLE 6

The second case, an eight year old spayed mixed-breed shepherd, was presented with history of weakness of rear legs and back of several months duration. She spent most of her time lying down, even when eating. After lying she was slow to stand and moved stiffly as if weak or in pain, she could not jump as she had in the past, and after brief exercise she would be reluctant to move and panted excessively. She winced in pain from pressure on the gluteal region. Spinal radiographs showed moderate lesions of spondyloarthopathy only at the lumbo-sacral junction. There appeared to be atrophy of masticatory and longissimus muscles, for bones of head and spinal processes were prominent. Blood count and serum chemistries were all within normal parameters. Indirect fluorescent-antibody tests with the dog's serum obtained on day one reacted against rat sciatic nerve tissue were negative, for antibodies against nerve tissue skeletal muscle tests showed a weak nonspecific response to muscle fibers but there was no reaction to connective tissue or vascular elements. A Hep-2 test for serum antinuclear antibodies was negative. Biopsy of longissimus muscle on day two at the level of lumbar vertebrae L2 and 3 revealed about half of muscle mass atrophied or replaced by fat. The possibility of immune-mediated myositis prompted therapeutic testing with prednisone and azathioprine for ten days, beginning on day seven. During the course of treatment there was a slight improvement in the dog's ability to move about but the response was considered inconclusive. Based on poor clinical response to immune suppression and negative indirect fluorescent antibody tests for antibodies to skeletal muscle it was concluded her malady probably was other than immune-mediated myositis. Longissimus muscle biopsy specimens became available on day thirteen. They substantiated the conclusion that the dog's muscle weakness was not an immune mediated myopathy for there was no inflammatory reaction in the muscle. Instead, there was both muscle fiber atrophy and metaplasia of satellite cells to lipocytes. There was no evidence of ragged red fibers as seen in humans with MELAS.

On day twenty-four, L-carnitine mg, per pound body weight orally twice daily in her food was prescribed. After three weeks of this treatment, the owner reported the dog was much stronger, now being able to jump into a pickup truck. She could walk and run about normally without apparent pain or panting and she could get to her feet quickly after lying down and no longer lay down to eat. The dog's condition continued to be satisfactory while receiving L-carnitine daily. To compare effectiveness and possible biochemical interchange of two nutrients, acetyl-L-carnitine was substituted for L-carnitine on day one-hundred. Sixteen days later the owner reported the dog's weakness, panting, and pain on palpation of gluteal region had returned. It was concluded L-carnitine but not acetyl-L-carnitine effectively relieved the dog's symptoms. To investigate compatibility and effectiveness of the combined nutrients L-carnitine and acetyl-L-carnitine were mixed in equal amounts and dispensed to be added to the dog's food, mg per pound body weight once daily. Following seven days of this therapy the owner telephoned to say the dog's activity and demeanor were again normal, the same as they had been when the dog was receiving L-carnitine and before acetyl-L-carnitine alone was given.

This example demonstrates beneficial effects of the invention when used to treat a dog with a previously undescribed skeletal myopathy. L-carnitine alone produced progressive improvement over a three week period before reaching a stable plateau. When acetyl-L-carnitine was substituted for carnitine the dog's previous clinical condition was reinstated in less than three weeks indicating Alcar was ineffective. However, the fact the invention elevated symptoms of muscle weakness and pain after one week of therapy indicates synergism between the two metabolic cofactors.

EXAMPLE 7

The third dog, a cardiac case when presented was clinically typical of other large dogs seen in practice that have a cardiac arrhythmia, usually ventricular tachycardia, often with unsatisfactory response, to medical management. This case illustrates, that in addition to cardiac disease, skeletal muscle weakness and epileptiform seizures can be manifest simultaneous in one dog and all respond to an oral supplement of combined L-carnitine and acetyl-L-carnitine.

The eight year old spayed Siberian Husky, when presented had a history of episodes of grand mall seizures, muscle weakness, and hypothyroidism, she was receiving levothyroxin Na daily. Initially, seizures occurred every few months when they began five years previously. No medical basis was found for the convulsions and there was no evidence of other central nervous dysfunction. When seizure frequency became more than one a month the owner sought medical assistance and the dog was treated with 25% KBr solution, 1 ml per 15 pounds body weight, orally once daily which controlled seizures.

Muscle weakness had been a progressive condition for three years. Other than an inconclusive superficial clinical examination for lameness no effort had been made to ascertain cause of the weakness. In her daily life prior to admittance she had become so weak she had to be supported with a sling under her belly whenever she walked more than twenty yards.

The day before admittance to the hospital the dog seemed to the owner to have a seizure. He considered the episode to be an atypical convulsion. Symptoms were described as disorientation, weakness, and collapse. When presented at the hospital the dog was unable to stand and walk. She had to be carried from the car into the hospital. On examination her pulse was weak and irregular. Her creatinine phosphokinase was four times higher than normal indicating probable heart muscle injury. An ECG showed long periods of ventricular tachycardia, a severe often fatal form of heart arrhythmia, with intermittent periods in which rhythm was normal but R wave magnitude was diminished. The dog's immediate problem was diagnosed as cardiac failure and the previous day's episode, which the owner witnessed, was considered to be syncope caused by an episode of ventricular tachycardia. The dog was treated with lidocaine and propanalol intravenously, with this standard treatment it was impossible to convert the arrhythmia. As a last resort she was treated orally with 500 mg sustained release procainamide and, because of beneficial cardiac response to combined L-carnitine and acetyl-L-carnitine with a previous case the combination was administered orally mg per pound body weight. The same treatment was administered that evening and the following morning. The ECG after twenty-four hours of treatment no longer showed evidence of ventricular tachycardia but was in other respects similar to the previous day. She was alert and responsive, still weak but as functional as she had been before the syncope episode. She was eating well so the L-carnitine, acetyl-L-carnitine combination was mixed in her food and continued morning and night for one week at which time her ECG was nearly normal and the procainamide was stopped and the L-carnitine and acetyl-L-carnitine combination was supplemented once daily. She showed no further heart related symptoms.

Just as the dog's cardiac function responded to the supplement her muscle weakness also improved. Four weeks after commencing treatment with L-carnitine and acetyl-L-carnitine the owner reported the dog was more active than she had been in several years, now free of all support she was able to run rapidly and happily about the house and go for long walks. The ECG, at that time, day twenty-eight was normal. In addition to heart and muscle function improvement, her nervous system had improved. Because of her good spirits it was decided to phase out seizure controlling medications. Three months after stopping all seizure control medication, her health continued to be good. She was very active, her haircoat, which had been rough and ragged, had become luxurious and she had one mild seizure once each month since treatment with L-carnitine and acetyl-L-carnitine began.

Numerous modifactions on variations in practice of the invention in its several aspects as above described are expected to occur such limitations as are set out in appended claims should be placed there on.

What is claimed is:

1. A method of treating a domesticated mammal or human in need of treatment, comprising the step of (a) administering to a domesticated mammal or human having a condition or conditions, related to dysfunctional energy metabolism that do not quickly or substantially permanently respond to L-carnitine or acetyl-L-carnitine alone, an effective amount of a preparation containing both L-carnitine and acetyl-L-carnitine, to substantially permanently alleviate the symptoms of or substantially cure the condition or conditions related to dysfunctional energy metabolism.

2. A method as recited in claim 1 wherein step (a) is practiced by administering daily a preparation containing at least about 2 milligrams each of both L-carnitine and acetyl-L-carnitine per pound of body weight of the domesticated mammal or human being treated.

3. A method as recited in claim 1 wherein step (a) is practiced so as to administer a preparation containing about 5 milligrams each of both L-carnitine and acetyl-L-carnitine per pound of body weight of the domesticated mammal or human being treated.

4. A method as recited in claim 1 wherein step (a) is practiced by adding the preparation of both L-carnitine and acetyl-L-carnitine to a dog's food so that the preparation is taken orally.

5. A method as recited in claim 1 wherein step (a) is practiced by administering the preparation of both L-carnitine and acetyl-L-carnitine parenterally.

6. A method as recited in claim 1 wherein step (a) is practiced with a ratio of L-carnitine to acetyl-L-carnitine of from about 1 to 2 to about 2 to 1.

7. A method as recited in claim 1 wherein step (a) is practiced by administering a preparation with approximately equal amounts of L-carnitine and acetyl-L-carnitine.

8. A method as recited in claim 1 wherein step (a) is also practiced by mixing preservative, stabilizing, coloring, or flavoring agents, or combinations thereof, to the preparation before it is administered, and by administering at least 2 milligrams per pound of body weight of the human or domesticated mammal being treated.

9. A pharmacological preparation for treating dysfunctional energy metabolism conditions, comprising a combined amount of both L-carnitine and acetyl-L-carnitine pharmacologically effective for treating dysfunctional energy metabolism conditions wherein the ratio of L-carnitine to acetyl-L-carnitine is from about 1 to 2 to about 2 to 1.

10. A pharmacological preparation as recited in claim 9 further comprising preservative, stabilizing, coloring, or flavoring agents, or combinations thereof.

11. A pharmacological preparation as recited in claim 9 wherein the preparation also contains an anti-caking agent and is in the form of a gelatin capsule for oral consumption.

12. A pharmacological preparation as recited in claim 9 wherein the effective ingredients of the preparation consist essential of L-carnitine and acetyl-L-carnitine.

13. A method of preventing dysfunctional energy metabolic conditions by practicing the step of: (a) administering to a human or domesticated mammal a prophylactic amount of a pharmacological preparation containing both L-carnitine and acetyl-L-carnitine effective to substantially prevent dysfunctional energy metabolic conditions.

14. A method as recited in claim 13 wherein step (a) is practiced by administering the preparation orally.

15. A method as recited in claim 14 wherein step (a) is further practiced by daily administering a preparation containing at least about 2 milligrams each of both L-carnitine and acetyl-L-carnitine per pound of body weight of the human or domesticated mammal being treated.

16. A method as recited in claim 14 wherein step (a) is further practiced using a ratio of L-carnitine to acetyl-L-carnitine from about 1 to 2 to about 2 to 1 in the preparation.

17. A method as recited in claim 14 wherein step (a) is further practiced using a preparation which also contains an anti-caking agent and is in the form of a gelatin capsule.

18. A method as recited in claim 14 wherein step (a) is practiced by administering the preparation in the form of a stable liquid aqueous solution containing, per milliliter volume, from 0.1 to 400 mg each of both L-carnitine and acetyl-L-carnitine.

19. A method as recited in claim 11 wherein step (a) is practiced using a formulation where the effective ingredients consist essentially of L-carnitine and acetyl-L-carnitine.

20. A method as recited in claim 1 wherein step (a) is practiced using a preparation with a ratio of L-carnitine to acetyl-L-carnitine of from about 1 to 40 to about 40 to 1, and a domesticated animal is treated.

* * * * *